US007163687B1

(12) United States Patent
Murphy et al.

(10) Patent No.: US 7,163,687 B1

(45) Date of Patent: Jan. 16, 2007

(54) STABILIZED PESTICIDE COMPOSITIONS

(75) Inventors: Dennis Lee Murphy, Flower Mound, TX (US); Jeanne Ann Witte, Carrollton, TX (US); Kim W. Yang, Dallas, TX (US)

(73) Assignee: Wellmark International, Schaumburg, IL (US)

(*) Notice: Subject to any disclaimer, the term of this patent is extended or adjusted under 35 U.S.C. 154(b) by 0 days.

(21) Appl. No.: 10/794,849

(22) Filed: Mar. 4, 2004

(51) Int. Cl.
*A01N 25/32* (2006.01)

(52) U.S. Cl. ...................... 424/410; 424/405; 424/406; 424/407; 424/417; 424/418; 424/419; 424/420; 424/421; 424/438; 424/442; 514/549

(58) Field of Classification Search ........ 424/405–410, 424/417–420, 421, 84, 125, 696, 724, 438, 424/442; 514/549, 552, 534, 536, 538
See application file for complete search history.

(56) References Cited

U.S. PATENT DOCUMENTS

| | | | | |
|---|---|---|---|---|
| 4,383,391 | A * | 5/1983 | Thomas et al. | 47/57.6 |
| 4,732,762 | A | 3/1988 | Sjogren | |
| 4,876,091 | A | 10/1989 | Clarke, Jr. | |
| 5,096,710 | A * | 3/1992 | Minagawa et al. | 424/405 |
| 6,001,382 | A * | 12/1999 | Levy | 424/405 |
| 6,613,138 | B1 * | 9/2003 | Welshimer et al. | 106/405 |
| 6,864,256 | B1 * | 3/2005 | Palma | 514/245 |
| 2002/0010156 | A1 * | 1/2002 | Kennedy et al. | 514/65 |

* cited by examiner

*Primary Examiner*—Neil S. Levy
(74) *Attorney, Agent, or Firm*—Townsend and Townsend and Crew LLP

(57) ABSTRACT

The present invention provides a shelf-life extending pesticide formulation, and methods of making and methods of use. The present invention prolongs the shelf-life many fold. In addition, methods of controlling insects on cattle are also provided.

22 Claims, 7 Drawing Sheets

Interrupting the Horn Fly Cycle

Mineral / Feed

LOT JM716, 0.01% IGR CATTLE MINERALS
FORMULATED WITH NEW CP2
STABILITY SCREEN -AMBIENT & 40°C
SPEC RANGE 0.0075 - 0.010 - 0.0125 w/w% (S)-Methoprene 0.015
0.0125
0.01
0.0075
0.005
0.0025
0

0 12 24 36 48 60 72 84 96 108 120 132 144 156 168
DAYS 0.011 0.011 0.011 0.0095 0.013 0.011 0.013 0.011 0.010 0.0097 0.012 0.0095

40C
AMBIENT

EXCELLENT

GOOD

AVERAGE TO BELOW

UNACCEPTABLE

STABILIZED PESTICIDE COMPOSITIONS

BACKGROUND OF THE INVENTION

Scientists estimate that horn flies (*haematobia irritans*) cost U.S. cattle producers $876 million each year. Together with fire ants and nuisance flies, they have a tremendously negative impact on the profits of farmers and ranchers in every industry.

Infestation occurs rapidly with 1000–4000 flies per animal in an untreated herd. In general, horn flies congregate on the back and shoulders of cattle, and tend to rest quietly on the host. Horn flies rarely leave their host, except to lay eggs, change host animals or remain outdoors when the host moves indoors.

Because they are a nuisance to the cattle, horn flies interrupt grazing patterns. The cattle tend to waste energy and even go off their feed. Due to horn flies infestations, calves are lighter at weaning by about 10–25 pounds. In addition, a 14% weight loss over 120 day fly period can amount to 26 lbs. per head. In the summer season, horn flies can cause 15–50 lbs. loss per head. At $0.90 per lb., a 30 lb. weight loss equals a $27.00 loss per head. Moreover, cows can go out of condition during breeding.

In view of the foregoing, there is a need for new more effective pesticide formulations and methods to control and treat flies, such as horn fly infestations in cattle. The present invention satisfies these and other needs.

SUMMARY OF THE INVENTION

The present invention provides inter alia, pesticide formulations used to control and treat fly infestation in cattle. Advantageously, the pesticide formulations have increased shelf-life. In fact, the pesticide formulations of the present invention prolong the shelf-life many fold. As such, the present invention provides a solid shelf-life extending pesticide formulation, comprising: a) a pesticide on a solid carrier; and b) a shelf-life extending agent, wherein the solid formulation is about 50 μm to amount 5 mm in size.

In still another embodiment, the present invention provides a method for producing a shelf-life extending pesticide formulation, comprising: a) providing a pesticide formulation; b) providing a shelf-life extending agent to produce an admixture; and c) processing the admixture to produce a solid formulation, wherein the solid formulation is about 50 μm to amount 5 mm in size.

In still yet another embodiment, the present invention provides a method for controlling an insect on cattle, comprising: administering a solid pesticide formulation as a feed-through product to cattle, wherein the solid formulation is about 50 μm to amount 5 mm in size; and allowing the feed-through product to pass through the cattle into manure, wherein the pesticide formulation is released in the manure to control the insect.

Advantageously, the present invention greatly improves the shelf-life of pesticides such as insect growth regulators in animal mineral feeds. Prior to the advent of the present invention, shelf-stability and shelf-life longevity was short. The present invention prolongs the shelf-life many fold. In addition, other advantages of the formulations of the present invention include reducing dustiness, reducing the electrostatic tendency of the final product, controlling the particle size during manufacture, taste masking, and decreased environmental toxicity for feed mill workers. These and other objects, embodiments and advantages will become more apparent when read with the drawings and detailed description which follow.

DETAILED DESCRIPTION OF THE INVENTION

I. General

Figure 1:
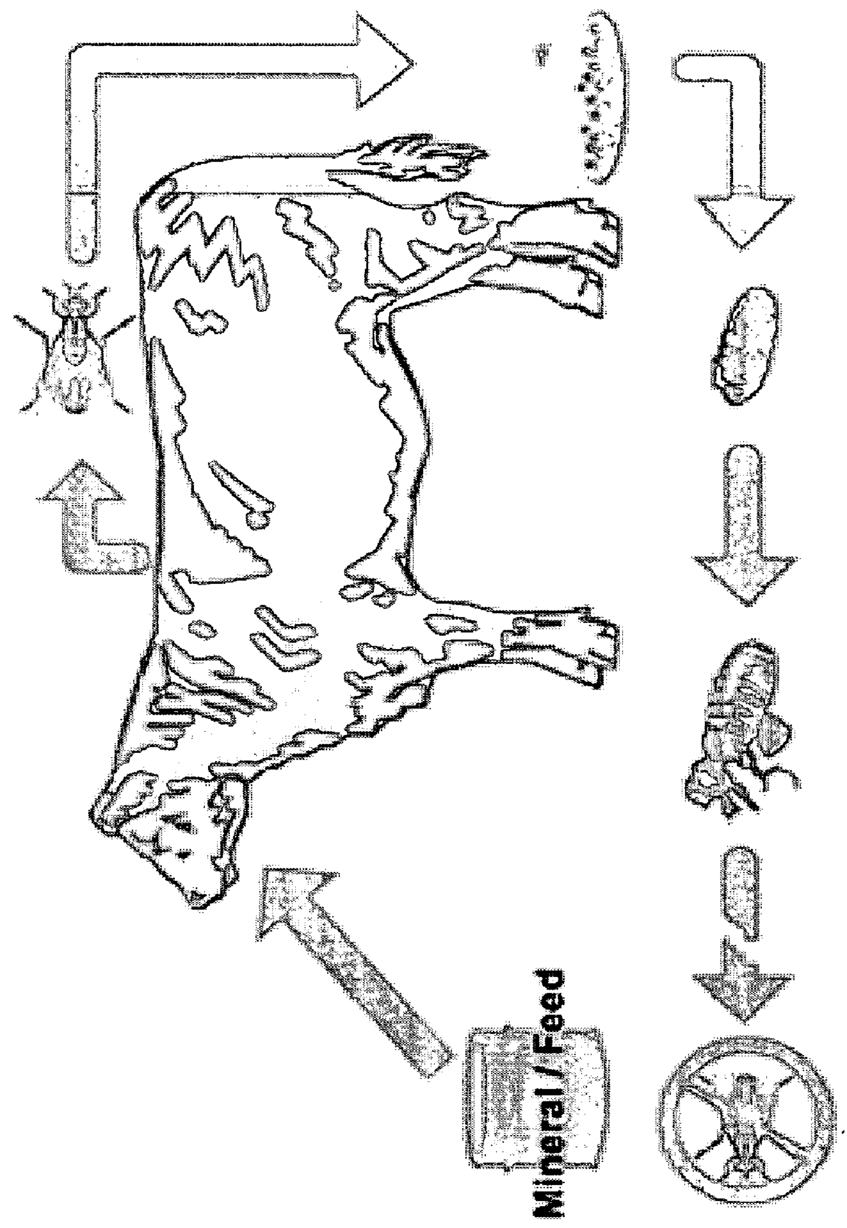
FIG. 1 shows a schematic of a use of the present invention.

The present invention provides pesticide formulations, methods of making pesticide formulations and methods of treating animals using the new pesticide formulations. The pesticide formulations have increased shelf-life. Advantageously, in certain aspects, the pesticide formulations of the present invention can be used in feed-through products to treat and control insect infestation in cattle. Various insects can be controlled and treated using the formulations and methods of the present invention. These include, but are not limited to, face flies, house flies, stable flies and horn flies. Horn flies are especially susceptible to the formulations and methods of the present invention.

II. Pesticides

Various pesticides can be used in the present invention. In a preferred aspect, the pesticide of the present invention is an insect growth regulator (IGR). Insect growth regulators (including juvenile hormones) are well known for their use and efficacy in controlling or eliminating insect infestation in humans, in animals, and in both residential and industrial environments. Many types of insects are controllable by insect growth regulators, including flies (e.g., face flies, house flies, stable flies and horn flies), fleas, mosquitoes, flour beetles, cigarette beetles, and cockroaches. The regulators vary widely in chemical composition, and two of the more prominent classes are 2,4-dienoic acids and phenoxyphenoxy compounds, particularly phenoxyphenoxyalkoxyheterocyclics, as well as benzoylureas and triazine derivatives. Examples of 2,4-dienoic acids and related compounds are methoprene, hydroprene, neotenin, and epiphenonane. As used herein, "methoprene" includes R-methoprene, S-methoprene and mixtures of R and S methoprene. S-methoprene is the preferred methoprene. Examples of phenoxyphenoxy compounds are fenoxycarb and pyriproxyfen. Examples of benzoylureas are lufenuron, diflubenzuron, terflubenzuron, triflumaron, hexaflumaron, and flucycloxuron. An example of a triazine derivative is 2-cyclopropylamino-4,6-bis(dimethylamino)-s-triazine.

The following IGR are suitable for the present invention. Chitin synthesis inhibitors are suitable such as bistrifluron, buprofezin, chlorfluazuron, cyromazine, diflubenzuron, flucycloxuron, flufenoxuron, hexaflumuron, lufenuron, novaluron, noviflumuron, penfluron, teflubenzuron, and triflumuron. In addition, juvenile hormone mimics are suitable such as epofenonane, fenoxycarb, hydroprene, kinoprene, methoprene, pyriproxyfen, and triprene. Further, juvenile hormones are suitable such as juvenile hormone I, juvenile hormone II, and juvenile hormone III. Other suitable IGRs include, molting hormone agonists, chromafenozide, halofenozide, and methoxyfenozide tebufenozide. Moreover, molting. hormones such as α-ecdysone, and ecdysterone are suitable. In addition, molting inhibitors such as diofenolan and other IGRs, which include precocenes, such as precocene I, precocene II, and precocene III are suitable. Finally, unclassified insect growth regulators are suitable such as dicyclanil. Preferred IGRs include methoprene, hydroprene, kinoprene, fenoxycarb, pyriproxifen, and mixtures thereof. In the most preferred embodiment, methoprene is the IGR of choice.

A. Carriers

In certain aspects, the pesticide of the present invention comprises a carrier such as a solid carrier. Solid carriers, which may be used for dusts, wettable powders, water dispersible granules, or granules, may be mineral fillers, such as calcite, silica, talc, kaolin, montmorillonite or attapulgite. The physical properties may be improved by addition of highly dispersed silica gel or polymers. Carriers for granules may be porous material, e.g. pumice, kaolin, sepiolite, bentonite; non-sorptive carriers include calcite or sand. Additionally, a multitude of pre-granulated inorganic or organic materials may be used, such as dolomite or crushed plant residues. Other suitable carriers include, but are not limited to, silica gel, sand, gypsum, charcoal and combinations thereof.

A practical material for the carrier of the pesticide is plaster of Paris which forms a gypsum-type product. The pesticide is intimately bonded with the plaster of Paris and is basically released when water dissolves the solid gypsum. Gypsum-based pesticides are known; for example, the product known as ALTOSID® made by Wellmark International Schaumberg, Ill., uses methoprene.

In certain aspects, the ratio of pesticide to carrier is about 0.001 to about 0.5 w/w. Preferably, the ratio of pesticide to solid carrier is about 0.01w/w to about 0.1 w/w.

In certain aspects, the formulations of the present invention are solid formulations. Such solid formulations can be for example, a granule, a particle, a pellet, a capsule (e.g., a microcapsule), a tablet, a whole feed ration, and combinations thereof. In one embodiment, the solid formulation is about 50 μm to amount 5 mm in size. More preferably, the size is 0.2 mm to amount 2 mm in size such as 0.3, 0.4, 0.5, 0.6, 0.7, 0.8, 0.9, 1.0, 1.1, 1.2, 1.3, 1.4, 1.5, 1.6, 1.7, 1.8, 1.9 and 2.0 mm. In one particular aspect, the solids are homogenous granules, filtered through wire mesh, such as 16 mesh or 40 mesh.

In other embodiments, the pesticide formations of the present invention comprise liquid carriers such as aromatic hydrocarbons, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or γ-butyrolactone, higher alkyl pyrrolidones, e.g. n-octylpyrrolidone or cyclohexylpyrrolidone, epoxidized plant oil or vegetable oil, or esters from fatty acids of vegetable oils, e.g. methylated coconut or soybean oil ester and water. Mixtures of different liquids are often suitable.

Pesticidal compositions are often formulated and transported in a concentrated form which is subsequently diluted by the user before application. The presence of small amounts of a carrier which is a surfactant facilitates this process of dilution. Thus, a carrier in the formulations according to the invention can be a surfactant. For example, the formulations can contain at least two or more carriers, at least one of which is a surfactant.

Surfactants can be nonionic, anionic, cationic or zwitterionic substances with good dispersing, emulsifying and wetting properties depending on the nature of the pesticide compound. Surfactants may also mean mixtures of individual surfactants.

B. Shelf-Life Extending Agent

In certain preferred aspects, the shelf-life extending agent is a carbohydrate (e.g. saccharide). Suitable carbohydrates include monosaccharides, oligosaccharides, polysaccharides and mixtures thereof. Suitable polysaccharides include, for example, a cyclodextrin, a starch, a carboxymethyl cellulose salt, an alginate, a methyl cellulose, an ethyl cellulose, a hydroxypropyl cellulose, sucrose, a starch glycolic acid salt, a molasses, lactose and dextrin. In certain aspects, the saccharide is a water soluble saccharide. In one preferred embodiment, the shelf-life extending agent is molasses. Suitable molasses includes, but is not limited to, beet sugar molasses, citrus molasses, hemicellulose extract, starch molasses, cane sugar molasses and combinations thereof. Those of skill in the art will know of other molasses suitable for use in the present invention.

In certain other aspects, the shelf-life extending agent is a cyclodextrin, such as an amorphous cyclodextrin as disclosed in U.S. Pat. No. 4,727,064. As disclosed therein, a cyclodextrin-based mixtures can be prepared from α-, β-, or γ-cyclodextrin which can be rendered amorphous through non-selective alkylation. The alkylation agents suitable for that purpose are exemplified by propylene oxide, glycidol, iodoacetamide, chloroacetate, or 2-diethylaminoethylchloride; their reactions with cyclodextrins were performed to yield mixtures containing many components, a circumstance which effectively prevents crystallization processes within the above pharmaceutical preparation.

In certain aspects, such as in a solid formulation, the ratio of the shelf-life extending agent to pesticide is about 100,000 to about 2:1, preferably, 40,000:1 to about 10,000:1, and more preferably, 5000:1 to about 2000:1 w/w.

In certain aspects, the shelf-life extending pesticide formulation further comprises a binding agent. Alternatively, the shelf-life extending agent is a binding agent.

In certain aspects, the shelf-life extending pesticide formulation further comprises a taste masking agent. Alternatively, the shelf-life extending agent is a taste masking agent.

In certain aspects, the formulations of the present invention further comprise an antioxidant. Suitable antioxidants include, but are not limited to, Vitamin E, Vitamin A palmitate, propyl gallate, butylated hydroxyanisole (BHA), butylated hydroxytoluene (BHT), and combinations thereof.

Surprisingly, the shelf-life extending agent such as molasses, will retard or prevent the degradation of some polymers and thermoplastics by methoprene. This advantageous property extends the shelf-life and broadens the variety of polymers and thermoplastics that can be used as packaging.

III. Methods of Making

In another embodiment, the present invention provides a method for producing a shelf-life extending pesticide formulation, comprising: a) providing a pesticide formulation; b) providing a shelf-life extending agent to produce an admixture; and c) processing the admixture to produce a solid form, wherein the solid formulation is about 50 μm to amount 5 mm in size. In certain aspects, the present invention improves the use of IGR methoprene granules to be used in other animal feed forms, such as pellets, cubes, complete feed ration and liquids.

Advantageously, the present formulations and methods reduce the dustiness of the IGR product such as methoprene granules. This advantage improves protection of the IGR methoprene from reacting with other minerals and ingredients found in animal feeds. In addition, the electrostatic tendency of the methoprene granules can be greatly reduced using the formulations and methods of the present invention. Moreover, the safety for feed mill workers has been increased as the toxicity of the environment has been reduced.

Moreover, the formulations and methods improve the ease of use/control for feed mill workers since it is free-flowing. (non-electrostatic) and masks any unpleasant taste of the IGR in animal feeds.

In one embodiment, methoprene with or without an antioxidant is sprayed on a mixing powder bed of dry molasses or sugar or other carbohydrate, liquid molasses (sugar, carbohydrate) or syrup (molasses, sugar, carbohydrate) is followed as a binder, and the admixture is then granulated, dried, and screened through a standard sieve or perforated plate to a desirable granule size. The formulations and methods of the present invention greatly improves the stability of the IGR and provides a longer shelf life.

Moreover, the formulations and methods improve the particle size control of the IGR granules so tendency to segregate from the animal feed components is minimized which in turn, improves uniformity throughout the feed.

In one embodiment, the compositions and formulations may be manufactured into e.g. emulsion concentrates, solutions, oil in water emulsions, wettable powders, soluble powders, suspension concentrates, dusts, granules, water dispersible granules, microcapsules, gels and other formulation types. These methods include intensive mixing and/or milling of the active ingredients with other substances, such as fillers, solvents, solid carriers, surface active compounds (surfactants), and optionally solid and/or liquid auxiliaries and/or adjuvants. The form of application such as spraying, atomizing, dispersing or pouring may be chosen like the compositions according to the desired objectives and the given circumstances.

The compositions and formulations of the present invention can for example, be formulated as wettable powders, water dispersible granules, dusts, granules, solutions, emulsifiable concentrates, emulsions, suspension concentrates and aerosols. Wettable powders usually contain 5 to 90% w/w of active ingredient and usually contain in addition to solid inert carrier, 3 to 10% w/w of dispersing and wetting agents and, where necessary, 0 to 10% w/w of stabilizer(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5 to 10% w/w of active ingredient. Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. The so-called "dry flowables" consist of relatively small granules having a relatively high concentration of active ingredient.

The formulations and compositions of the present invention may in certain aspects, comprise other additives such as defoamers, corrosion inhibitors, stabilizers, penetrants and retention enhancers (stickers), and water or an organic liquid in which the active ingredient is substantially insoluble; certain organic solids or inorganic salts may be present dissolved in the formulation to assist in preventing sedimentation and crystallization or as antifreeze agents for water.

In still other aspects, the present invention provides aqueous dispersions and emulsions, for example compositions obtained by diluting the formulated product with water.

In certain other aspects, the biological activity of the active ingredient can be increased by including an adjuvant. An adjuvant is defined here as a substance which can increase the biological activity of an active ingredient but is not itself significantly biologically active. The adjuvant can either be included in the formulation as a co-formulant or carrier, or can be added to the formulation containing the active ingredient.

IV. Uses

In still other embodiments, the present invention provides a method for controlling or treating an insect on an animal such as cattle. As shown in FIG. 1, the method includes administering a pesticide formulation as a feed-through product to the animal, wherein the pesticide formulation is formulated into a final form such as a granule, a particle, a pellet, a capsule such as a microcapsule, a cube, a tablet such as a microtablet, a complete feed ration and combinations thereof. The feed-through product is allowed to pass through the animal into its manure. The pesticide formulation is released in the manure, thereby controlling the insect.

Figure 2:
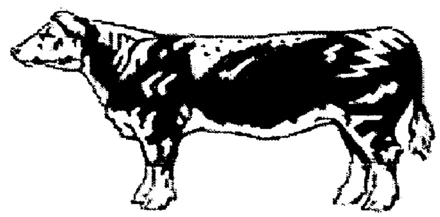
FIG. 2 shows a schematic of various degrees of horn fly infestation on cattle.
Figure 2:
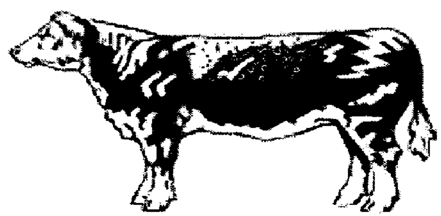
Figure 2:
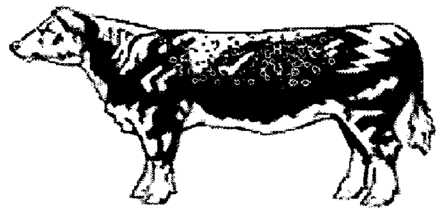
Figure 2:
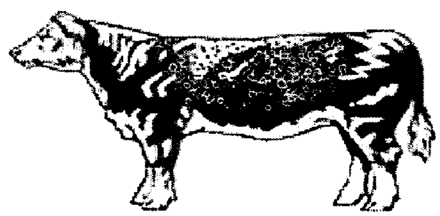

Turing now to FIG. 2, in one example, cattle are unacceptably infested with horn flies. Adult horn flies live 2 to 4 weeks taking 20 to 30 blood meals a day from the cattle. The pesticide formulation of the present invention is ingested with the cattle's mineral or feed. As they graze, cattle disperse the IGR via their manure. The compositions of the present invention breaks the life cycle of the horn fly, by for example, preventing pupae from molting into adults. In 1 to 2 days, eggs hatch into larvae. After 3 to 5 days, the larvae molt into pupae. Preferably, the composition of the present invention, such as an IGR composition, prevents adult emergence following pupal stage.

V. Examples

1. EXAMPLE 1

This Example illustrates a storage stability study of five lots of 0.01% IGR mineral feed that were formulated with Altosid® (CP-10). These five lots (JM534, JM535, JM536, JM537, and JM538) do not comprise a shelf-life extending agent. Lot JM716 (Altosid® CP-2) is made in accordance to the present invention and comprises a shelf-life extending agent.

Figure 3:
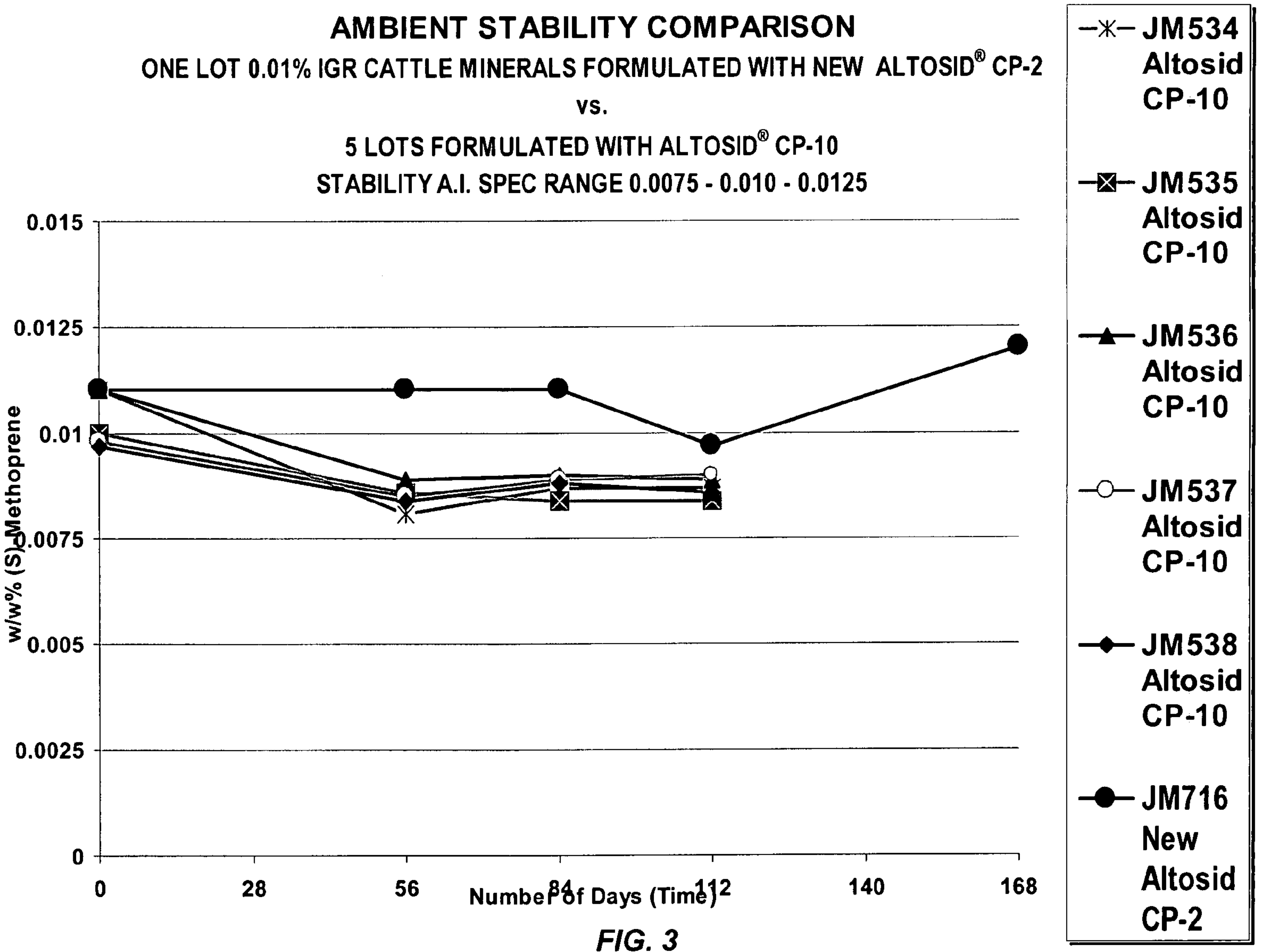
FIG. 3 shows shelf-life comparison data of an embodiment of a pesticide formulation of present invention versus other pesticide formations.
Figure 4:
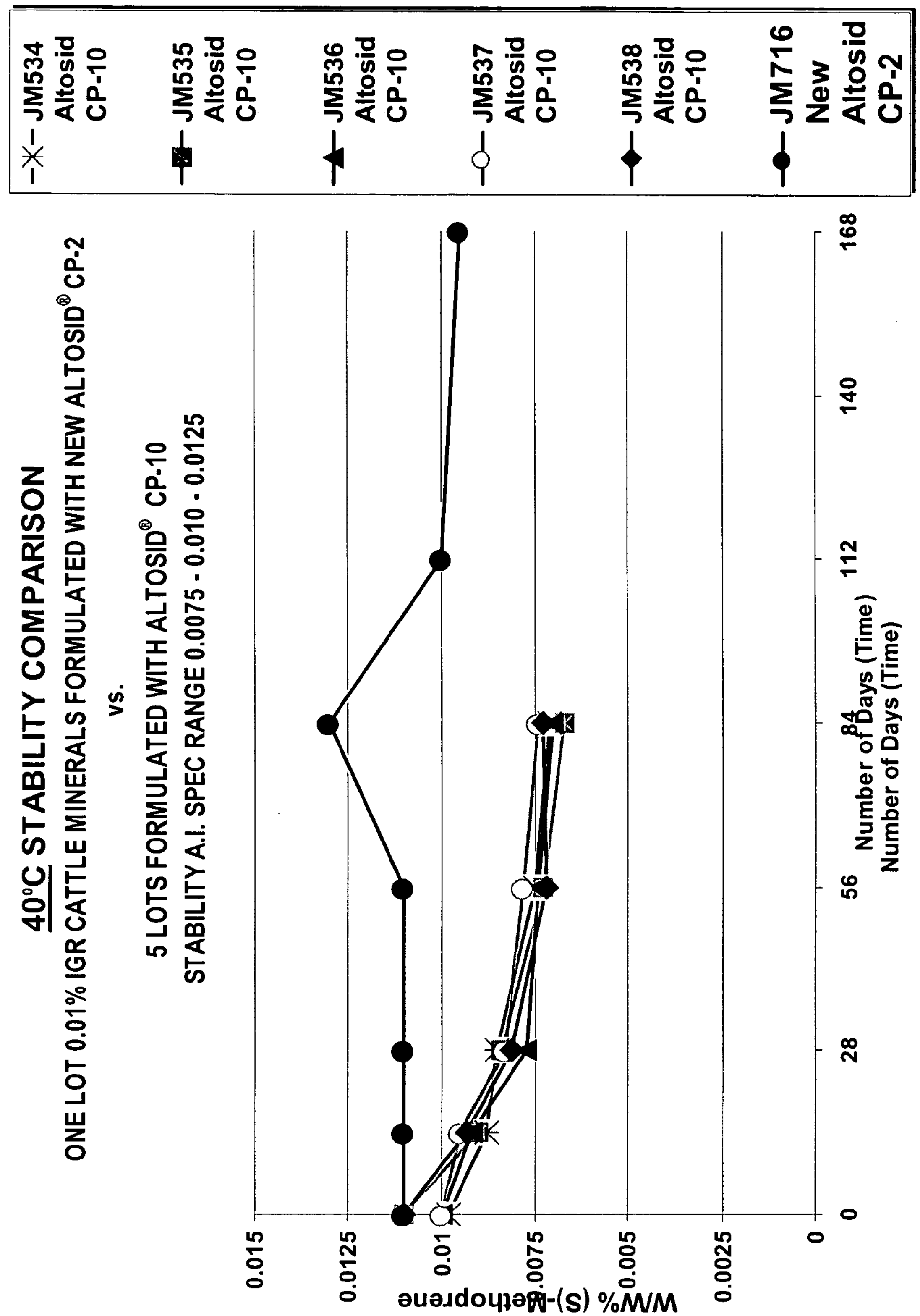
FIG. 4 shows shelf-life comparison data of an embodiment of a pesticide formulation of present invention versus other pesticide formations.

Storage conditions are compared at ambient temperature and 40° C. and all lots were stored in KRAFT bags with the ends sewn closed. All bags were sampled and the results are in w/w % for (S)-methoprene as a function of time. Each lot was tested at the time interval (0, 14, 28, 56 and 84 days) as indicated using liquid chromatography. The samples were tested at ambient temperature (FIG. 3) as well as at 40° C. (FIG. 4). The lot of the present invention (JM716 Altosid® CP-2) is superior in chemical stability and physical stability.

Altosid® CP-10 composition is 10.5% of the active ingredient (S)-Methoprene applied onto a solid carrier, plus non-hazardous inert ingredients to create a very fine dusty product. Altosid® CP-2 composition is 2% of the active ingredient (S)-Methoprene applied onto dried molasses (saccharides/carbohydrates), plus non-hazardous inert ingredients to create a non-dusty, flow-able, granular product. In this case, the ratio of the molasses to methoprene is 35:1 w/w. As such, Altosid® CP-10 is lacking the saccharide/carbohydrate that Altosid® CP-2 contains.

TABLE I

| Ambient | 0 | 56 | 84 | 112 | 84 | 112 | 168 |
|---|---|---|---|---|---|---|---|
| JM534 Altosid CP-10 | 0.011 | 0.0081 | 0.0087 | 0.0087 | | | |
| JM535 Altosid CP-10 | 0.010 | 0.0086 | 0.0084 | 0.0084 | | | |
| JM536 Altosid CP-10 | 0.011 | 0.0089 | 0.0090 | 0.0089 | | | |
| JM537 Altosid CP-10 | 0.0098 | 0.0085 | 0.0089 | 0.0090 | | | |
| JM538 Altosid CP-10 | 0.0097 | 0.0084 | 0.0088 | 0.0086 | | | |
| JM716 Altosid CP-2 | 0.011 | 0.011 | 0.011 | 0.0097 | 0.011 | 0.0097 | 0.012 |
| **40° C.** | **0** | **14** | **28** | **56** | **84** | **112** | **168** |
| JM534 Altosid CP-10 | 0.0098 | 0.0088 | 0.0085 | 0.0075 | 0.0071 | | |
| JM535 Altosid CP-10 | 0.011 | 0.0090 | 0.0084 | 0.0073 | 0.0067 | | |
| JM536 Altosid CP-10 | 0.010 | 0.0092 | 0.0077 | 0.0074 | 0.0070 | | |
| JM537 Altosid CP-10 | 0.010 | 0.0095 | 0.0083 | 0.0078 | 0.0074 | | |
| JM538 Altosid CP-10 | 0.011 | 0.0093 | 0.0081 | 0.0072 | 0.0073 | | |
| JM716 Altosid CP-2 | 0.011 | 0.011 | 0.011 | 0.011 | 0.013 | 0.010 | 0.0095 |

2. EXAMPLE 2

This example illustrates a 8-week storage stability study for three lots (JM 705, JM706, and JM707) of 0.01% IGR minerals formulated with Altosid® Concentrate (CP-10) compared to one lot of 0.01% IGR mineral formulated with CP-2 (JM716). Three lots (JM705, JM706 and JM707) do not comprise a shelf-life extending agent. Lot JM716 (Altosid® CP-2) is made in accordance to the present invention and comprises a shelf-life extending agent. Storage conditions for all lots are compared at ambient temperature and 40° C. Lots were stored in KRAFT bags with the ends sewn closed. All bags were sampled and the results are in w/w % for (S)-Methoprene as a function of time.

Figure 5:
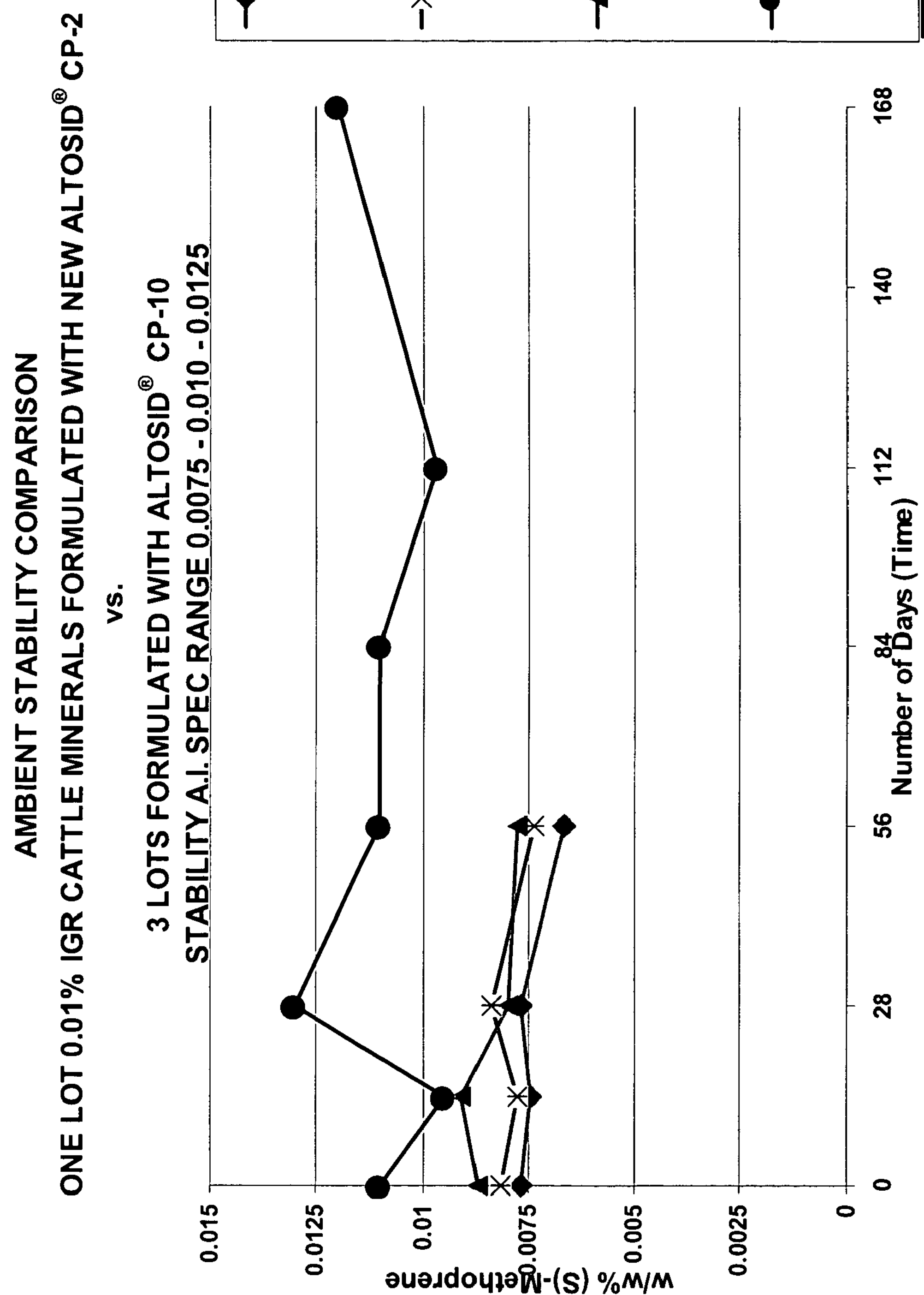
FIG. 5 shows shelf-life comparison data of an embodiment of a pesticide formulation of present invention versus other pesticide formations.
Figure 6:
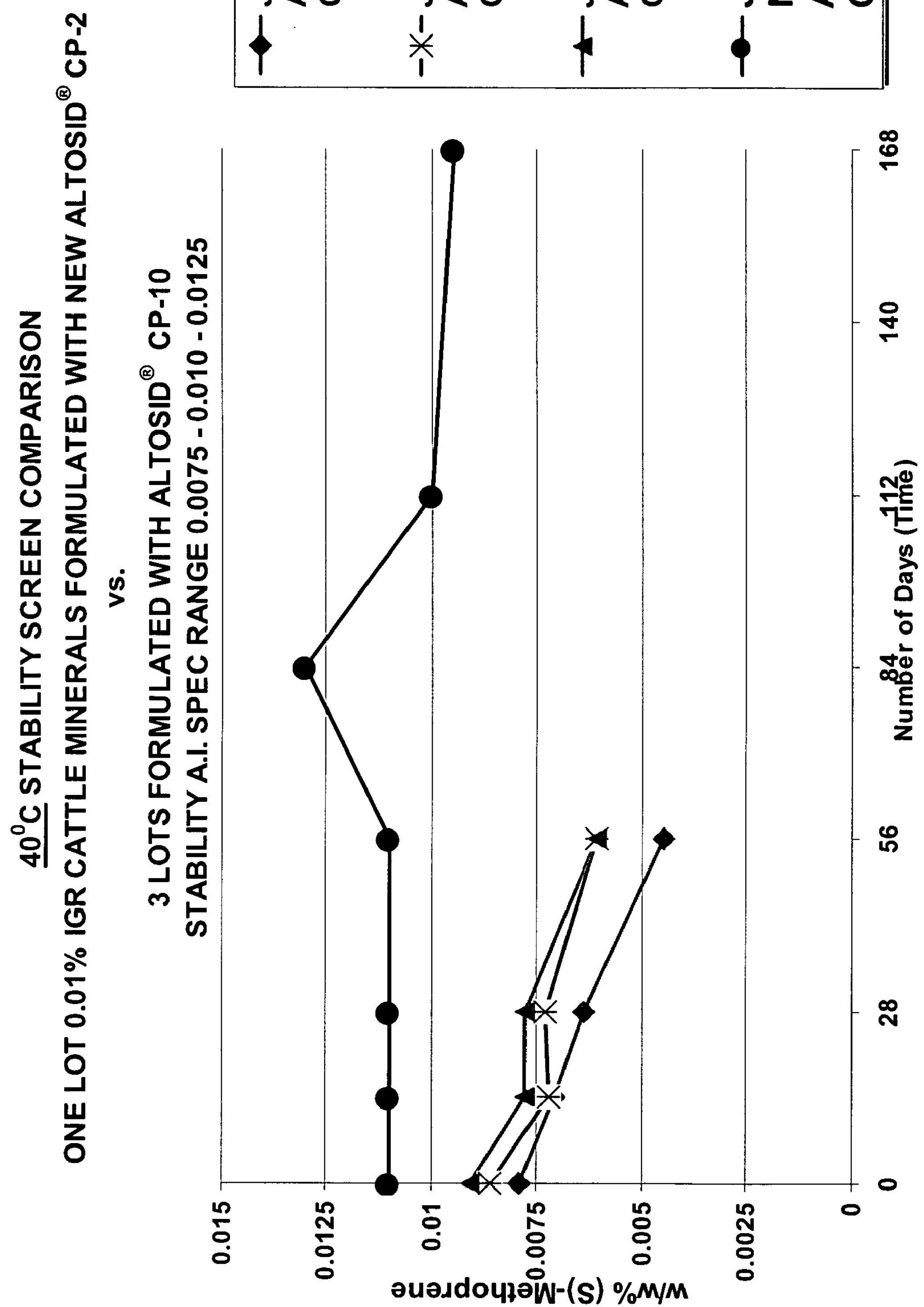
FIG. 6 shows shelf-life comparison data of an embodiment of a pesticide formulation of present invention versus other pesticide formations.

Each lot was tested at the time interval (0, 14, 28, and 56 days) as indicated using liquid chromatography. The samples were tested at ambient temperature (FIG. 5) as well as at 40° C. (FIG. 6). The lot of the present invention (JM716 Altosid® CP-2) is superior in chemical stability and physical stability.

TABLE 2

| Ambient | 0 | 14 | 28 | 56 | 84 | 112 | 168 |
|---|---|---|---|---|---|---|---|
| JM705 Altosid CP-10 | 0.0077 | 0.0075 | 0.0077 | 0.0067 | | | |
| JM706 Altosid CP-10 | 0.0082 | 0.0078 | 0.0084 | 0.0074 | | | |
| JM707 Altosid CP-10 | 0.0087 | 0.0091 | 0.0080 | 0.0078 | | | |
| JM716 Altosid CP-2 | 0.011 | 0.0095 | 0.013 | 0.011 | 0.011 | 0.0097 | 0.012 |
| **40 C.** | **0** | **14** | **28** | **56** | **84** | **112** | **168** |
| JM705 Altosid CP-10 | 0.0079 | 0.0071 | 0.0064 | 0.0045 | | | |
| JM706 Altosid CP-10 | 0.0086 | 0.0072 | 0.0073 | 0.0061 | | | |
| JM707 Altosid CP-10 | 0.0091 | 0.0078 | 0.0078 | 0.0061 | | | |
| JM716 Altosid CP-2 | 0.011 | 0.011 | 0.011 | 0.011 | 0.013 | 0.010 | 0.0095 |

Duplicate samples were assayed and results under each lot are in w/w % for (S)-Methoprene.
All lots were stored in KRAFT bags with the ends sewn closed.

3. EXAMPLE 3

Figure 7:
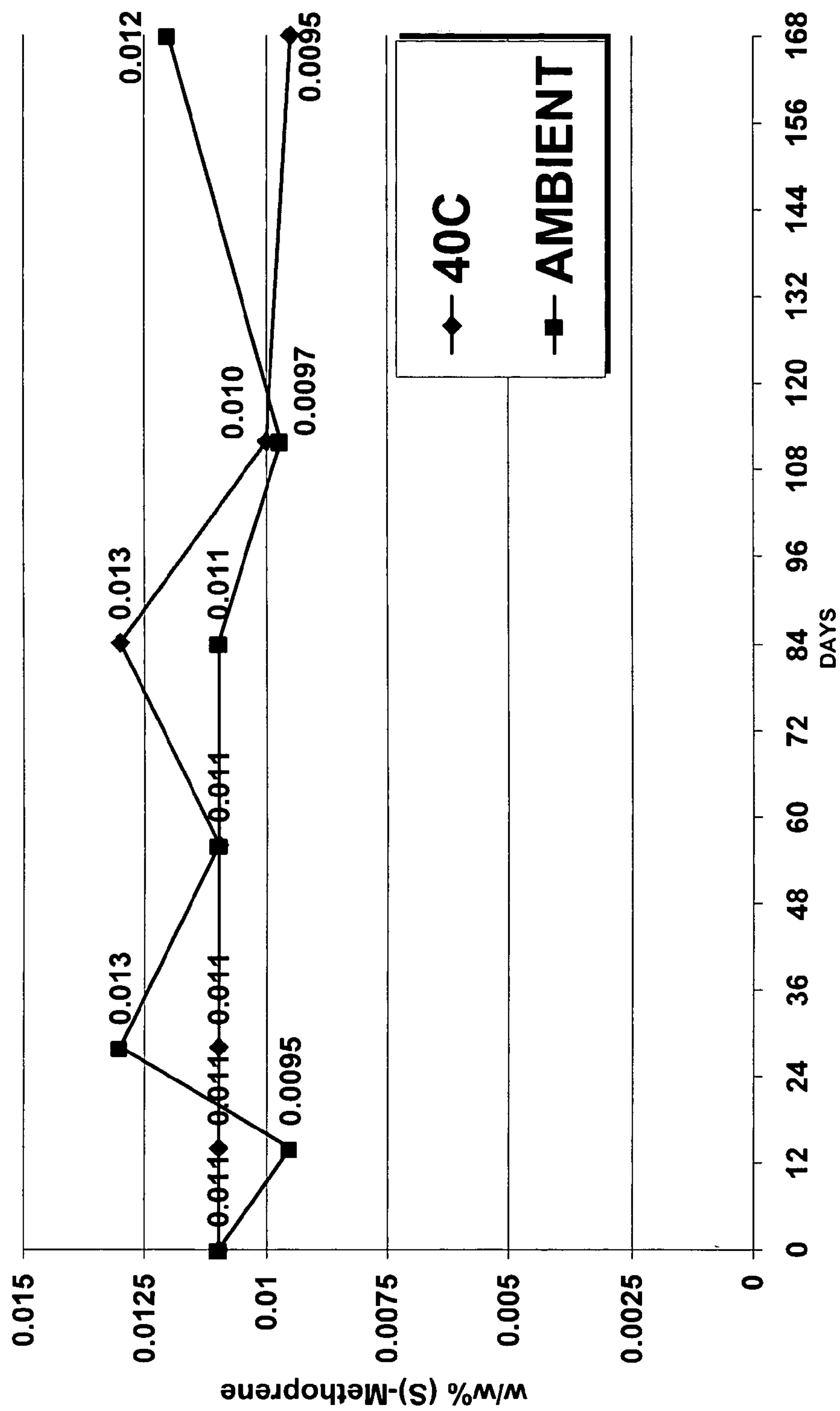
FIG. 7 shows stabilization data of an embodiment of a pesticide formulation of present invention.

This example illustrates the stability of a formulation of the present invention using molasses as the shelf-life extending agent. The lot was tested at the time interval (0, 14, 28, 56, 84, 112, and 168 days) indicated using liquid chromatography. The samples were tested at ambient temperature as well as at 40° C. (FIG. 7). The present invention (JM716 Altosid® CP-2) shows excellent chemical stability and physical stability.

TABLE 3

| | 0 | 14 | 28 | 56 | 84 | 112 | 168 |
|---|---|---|---|---|---|---|---|
| 40° C. | 0.011 | 0.011 | 0.011 | 0.011 | 0.013 | 0.010 | 0.0095 |
| AMBIENT | 0.011 | 0.0095 | 0.013 | 0.011 | 0.011 | 0.0097 | 0.012 |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A solid shelf-life extending pesticide formulation, said formulation consisting essentially of:

a) methoprene on a solid carrier wherein said solid carrier is selected from the group consisting of silica gel and charcoal; and b) molasses, wherein said solid formulation is formulated as a feed-through animal product of about 50 μm to about 5 mm in size and the ratio of said molasses to said methoprene is about 100,000:1 w/w to about 2:1 w/w.

2. The formulation of claim 1, wherein said formulation is about 0.2 mm to about 2 mm in size.

3. The formulation of claim 1, wherein the ratio of said molasses to methoprene is about 40,000:1 to about 10,000:1 w/w.

4. The formulation of claim 1, wherein the ratio of said molasses to methoprene is about 5000:1 to about 2000:1 w/w.

5. The formulation of claim 1, wherein the ratio of said molasses to said methoprene is about 2000:1 to about 2:1 w/w.

6. The formulation of claim 1, wherein the ratio of said molasses to said methoprene is about 35:1 to about 2:1 w/w.

7. A solid shelf-life extending pesticide formulation of claim 1, wherein, the ratio of molasses to said methoprene is about 35:1.

8. The formulation of claim 1, wherein the ratio of methoprene to solid carrier is about 0.001 to about 0.5% w/w.

9. The formulation of claim 8, wherein the ratio of methoprene to solid carrier is about 0.01 to about 0.1% w/w.

10. The formulation of claim 1, wherein said molasses is a binding agent.

11. The formulation of claim 1, wherein said formulation further comprises an antioxidant.

12. The formulation of claim 11, wherein said antioxidant is selected from the group consisting of Vitamin E, Vitamin A palmitate, propyl gallate, butylated hydroanisole (BHA), butylated hydroxytoluene (BHT), and combinations thereof.

13. The formulation of claim 1, wherein shelf-life extending pesticide is formulated into a final form selected from the group consisting of a granule, a particle, a pellet, a capsule, a tablet and combinations thereof.

14. A method for controlling an insect on a cattle, said method comprising:

administering a solid pesticide formulation of claim 1 to cattle; and allowing said feed-through product to pass through said cattle into manure, wherein the pesticide formulation is released into the manure thereby controlling said insect.

15. The method of claim 14, wherein said molasses is a member selected from the group consisting of beet sugar molasses, citrus molasses, hemicellulose extract, starch molasses, cane sugar molasses and combinations thereof.

16. A solid shelf-life extending pesticide formulation, said formulation consisting essentially of:

a) methoprene sprayed on dry molasses; and b) a molasses binder, wherein said solid formulation is granulated as a feed-through animal product to a granule of about 50 μm to about 5 mm in size and having a ratio of said molasses to methoprene is about 100,000:1 w/w to about 2:1 w/w.

17. The formulation of claim 1, 7, or 16, wherein said molasses is a member selected from the group consisting of beet sugar molasses, citrus molasses, hemicellulose extract, starch molasses, cane sugar molasses and combinations thereof.

18. The formulation of claim 1, 7, or 16, wherein said formulation contains between 0.5 to 10% w/w methoprene.

19. The formulation of claim 1, 7, or 16, wherein said formulation contains 2% w/w methoprene.

20. The formulation of claim 1, 7, or 16, wherein said formulation contains 0.02% w/w methoprene.

21. The formulation of claim 1, 7, 16 wherein said formulation contains 0.01% w/w methoprene.

22. The formulation of claim 1, 7, or 16, wherein said formulation contains 0.0025% methoprene.

* * * * *